United States Patent [19]

Joshi et al.

[11] Patent Number: 5,252,318
[45] Date of Patent: Oct. 12, 1993

[54] REVERSIBLE GELATION COMPOSITIONS AND METHODS OF USE

[75] Inventors: Abhay Joshi; Shulin Ding; Kenneth J. Himmelstein, all of Irvine, Calif.

[73] Assignee: Allergan, Inc., Irvine, Calif.

[21] Appl. No.: 539,061

[22] Filed: Jun. 15, 1990

[51] Int. Cl.$^5$ .................. A61K 31/19; A61K 31/745; A61K 47/38; A01N 25/04
[52] U.S. Cl. .......................... 424/78.04; 424/422; 424/427; 424/428; 424/2; 514/912; 514/913; 514/914; 514/915
[58] Field of Search ................. 424/2, 422, 78.04; 514/912, 913, 914, 915

[56] References Cited

U.S. PATENT DOCUMENTS

| | | | |
|---|---|---|---|
| 4,271,143 | 6/1981 | Schoenwald et al. | 424/78 |
| 4,407,792 | 10/1984 | Schoenwald et al. | 424/81 |
| 4,474,751 | 10/1984 | Haslam et al. | 424/78 |
| 4,474,752 | 10/1984 | Haslam et al. | 424/78 |
| 4,474,753 | 10/1984 | Haslam et al. | 424/78 |
| 4,615,697 | 10/1986 | Robinson | 424/428 |
| 4,692,454 | 9/1987 | Mich et al. | 514/312 |
| 4,911,920 | 3/1990 | Jani et al. | 424/78 |

FOREIGN PATENT DOCUMENTS

| | | |
|---|---|---|
| 0075540 | 3/1983 | European Pat. Off. . |
| 0227494 | 7/1987 | European Pat. Off. . |
| 0300888 | 1/1988 | European Pat. Off. . |
| 3440352 | 5/1986 | Fed. Rep. of Germany ...... 514/915 |
| 00451 | 8/1989 | PCT Int'l Appl. . |

Primary Examiner—Thurman K. Page
Assistant Examiner—Carlos Azpury
Attorney, Agent, or Firm—Poms, Smith, Lande & Rose

[57] ABSTRACT

Reversibly gelling aqueous compositions are disclosed which undergo significant changes in viscosity in response to substantially simultaneous changes in both temperature and pH. The compositions are formed of relatively low concentrations of a stable combination of at least one pH-sensitive reversibly gelling polymer and at least one temperature-sensitive reversibly gelling polymer. The compositions can be formulated to exhibit a sol-gel transition over a wide range of conditions and viscosities and may be modified to incorporate a pharmaceutical compound for utilization as droppable or injectable drug delivery systems which will gel following administration to a physiological system for the sustained delivery of such pharmaceutical compounds.

39 Claims, 4 Drawing Sheets

REVERSIBLE GELATION COMPOSITIONS AND METHODS OF USE

FIELD OF THE INVENTION

The present invention relates in general to macromolecular polymer mixtures exhibiting reversible gelation properties. More particularly, the present invention is directed to aqueous compositions that reversibly gel in response to simultaneous variations in at least two physical parameters such as temperature and pH or ionic strength. These compositions can be designed to reversibly gel at varying viscosities over a relatively wide range of conditions, making them particularly suitable for use as droppable, oral, or injectable drug delivery systems for the sustained and controlled delivery of pharmaceutical medicaments and diagnostic agents.

BACKGROUND OF THE INVENTION

Various approaches to the production of reversibly gelling solutions have been developed over the years. Principal efforts have been devoted to the development of gelatinous drug delivery systems for topical and subcutaneous applications and, more recently, for the administration of ophthalmic drugs to the eye. In general, sustained release drug delivery systems incorporate pharmaceutical agents in solid or semi-solid vehicles which are applied to or implanted under the skin of a patient by medical personnel. Additionally, unlike conventional drug delivery systems, ocular drug delivery systems also must address the additional problem of drug loss through the lacrimal drainage system as well as the needs of patient comfort and ease of administration.

Early approaches to the solution of the problems associated with ocular drug delivery systems utilized semi-solid ointments or gels applied directly to the conjunctive or cul-de-sac of the eye to retain the pharmaceutical agents contained therein on the ocular surface against such physiological factors as tear turnover, tear drainage, blinking, and other mechanical losses. For example, U.S. Pat. Nos. 3,944,427 and 3,700,451 disclose gelatinous drug delivery compositions containing agar, xanthine gum, and carob gum in liquid mediums in order to enhance their residence time upon the skin or mucosas and the resultant bioavailability of the medicinal products contained therein. Similarly, European Patent Application No. 0 300 888 A1, filed Jul. 18, 1988, recently disclosed the use of rhamsan gum to thicken ophthalmic compositions for droppable and topical application.

Though effective at increasing drug retention times, lack of patient acceptability remains as a significant drawback to the use of such known viscous drug delivery compositions in the eye. Many patients experience difficulty in applying the appropriate amount of such compounds to the eye and resist the unpleasant side effects of eyelid crusting and vision blurring. As a result, these compounds may only be suitable for use in the evening or during non-active hours.

A known alternative approach to these problems was the use of a formulation which is liquid at room temperature but which forms a semisolid solid when warmed to body temperature. Such a thermally triggered system is disclosed in U.S. Pat. No. 4,474,751, where an aqueous drug delivery system that forms a semi-solid "gel" at body temperature is formed from proprietary polymers known as "Tetronic ®" polyols. Generally speaking, these compositions are formed from approximately 10% to 50% of the specific polymers in an aqueous base. By adjusting the pH of these drug delivery systems through the addition of buffering agents, the gelling transition temperature can be raised to physiological temperatures on the order of 35° C.

Similar drug delivery systems which can be injected subcutaneously or intramuscularly are disclosed in U.S. Pat. No. 4,474,752. These compounds also contain from 10% to 50% by weight Tetronic ® polymers and gel at temperatures from about 30° to 100° C.

A thermal setting gel drug delivery system is also described in U.S. Pat. No. 4,188,373, utilizing "Pluronic ® polyols" as the thermally gelling polymer. Adjusting the concentration of the polymer gives the desired "sol-gel" transition temperature. However, producing a compound which sets at physiologically useful temperature ranges limits the available viscosity of the gelled product.

Alternatively, it has been proposed to utilize formulations which gel in response to changes in pH as drug delivery vehicles. By carefully controlling the pH of such mixtures, a solution which forms a gel upon mixing with aqueous tear fluid could theoretically be produced. However, it is believed that the relatively high buffering capacity of such pH responsive compositions can lead to slow gelling, irritation and discomfort in patient eyes.

Though successful at achieving increased drug retention times, the relatively high polymer concentrations required by such formulations undesirably increase both the buffering capacity and the amount of thermal energy necessary to induce gelation of the compounds which may lead to irritation and discomfort when used in the eye. What is more, the high polymer concentrations also contribute to unacceptably high product costs and generally slow the gelling process as well, leading to migration of the compounds from the site of application or injection.

Accordingly, it is a principal object of the present invention to provide a reversibly gelling polymer solution having significantly lower polymer concentrations than has previously been attainable by the prior art in order to reduce both the buffering and thermal capacities of the solution to ensure its rapid and complete transition from liquid to gel upon application to a physiological system such as an oral dosage, the surface of the eye, or an injectable drug depot.

It is a further object of the present invention to provide a reversibly gelling solution which can be utilized as a drug delivery vehicle or wetting solution that can easily be administered by a patient in the form of a freely flowing liquid or drops which gel immediately following administration with minimal side effects, thereby providing ready patient control of drug dosage and improved patient acceptability.

It is a further object of the present invention to provide an oral dosage, drop-instillable, injectable or other depot form drug delivery vehicle which will prolong drug contact time for improved bioavailability and for sustained drug release.

SUMMARY OF THE INVENTION

Generally stated, the present invention accomplishes the above-described objectives by providing aqueous compositions that reversibly gel in response to substantially simultaneous variations in at least two physical parameters such as temperature, pH, or ionic strength. What is more, the compositions of the present invention can be tailored to exhibit a specific sol-gel transition over predetermined temperature and pH ranges to make the compositions particularly well suited for use as drop-instillable aqueous wetting agents and drug delivery systems, as well as for use as injectable sustained release drug delivery systems.

More particularly, it has been surprisingly discovered that superior reversibly gelling compositions can be produced from unusually low concentrations of uniquely synergistic polymer systems which stably exist in aqueous solutions. In contrast to prior art gelation systems that rely on only a single triggering mechanism which may be either changes in pH, ionic strength, or changes in temperature, the compositions of the present invention reversibly gel in response to substantially simultaneous changes in both temperature and pH over predetermined ranges. What is more, the synergistic gelation action of the compositions of the present invention produces rapid and complete viscosity changes of an order of magnitude without the undesirable side effects associated with the high polymer concentration, single gelation mechanism compositions of the prior art.

These properties make the compositions of the present invention particularly well suited for uses as topically applied lubricants and wetting agents as well as for drug delivery vehicles where sustained and controlled delivery of bioactive agents is desired. For example, wetting agents, ocular drug delivery vehicles, oral and injectable drug delivery compositions can be produced in accordance with the teachings of the present invention which exhibit steady state flow characteristics at or near room temperature and a pH range of 2.5 to 6.5, yet almost instantaneously transform to highly viscoelastic gels when exposed to physiological conditions of pH and temperature on the order of pH 7.4 and 37° C.

Exemplary compositions are formed in accordance with the teachings of the present invention from aqueous solutions containing effective concentrations of a stable physical admixture or combination of at least one thermally-sensitive gelling polymer and at least one pH-sensitive gelling polymer. Thermally-sensitive gelling polymers for practicing the present invention can be selected from the group including alkyl cellulose, hydroxyalkyl cellulose, cellulosic ethers, Pluronic ® polymers and Tetronic ® polymers, with methylcellulose being particularly preferred. Exemplary pH-triggered gelling polymers that produce thickening at increased pH are preferably acidic polymers such as those containing carboxyl groups. Those skilled in the art will appreciate that small amounts of crosslinking agents such as divinyl benzene, divinyl glycol and polyalkenyl polyethers will facilitate the formation of three dimensional polymer network structures in the resultant cross-linked polyacrylates. Carboxy vinyl linear or branched or cross-linked polymers of the monomers, such as methacrylic acid, ethacrylic acid, β-methylacrylic acid, cis-α-methylcrotonic acid, trans-α-methylcrotonic acid, α-butylcrotonic acid, α-phenylacrylic acid, α-benzylacrylic acid, α-cyclohexylacrylic acid, and the like are examples of such acidic pH-sensitive gelling polymers. Conversely, where thickening is desired at decreased pH, polymers containing weakly basic pendant groups such as poly-N-N-dimethylaminoethylmethacrylate may be employed.

In contrast to the relatively high polymer concentrations required by the individually triggered prior art compositions (on the order of 10% or more by weight), the reversibly gelling compositions of the present invention preferably contain only approximately 0.25% to 5% by weight thermally-sensitive gelling polymer and only 0.1% to 0.5% by weight pH-sensitive gelling polymer. This substantially lower polymer concentration significantly reduces the amount of thermal energy required to induce gelation as well as reducing the buffering capacity of the compositions of the present invention, making them markedly superior topical wetting agents and drug delivery compounds. When utilized in the ocular milieu, the compositions of the present invention eliminate the discomfort, vision blurring and crusting produced by the known prior art compositions yet produce rapid conformational changes to high viscosity.

However, it is contemplated as being within the scope of the present invention to utilize thermally-sensitive gelling polymer concentrations ranging from approximately 0.1% to 30% by weight and pH-sensitive gelling polymer concentrations ranging from approximately 0.01% to 10% by weight. As discussed in detail below, these relatively broader polymer concentration ranges increase the scope of the available viscosities and sol-gel transition temperatures that may be produced in accordance with the teachings of the present invention. Thus, viscosities ranging from 200 to approximately 1 million cP at sol-gel transition temperatures ranging from 0° C. to 60° C. can be attained with the present invention. Nonetheless, for ophthalmic uses, the previously described polymer concentration ranges are preferred.

For use as drug delivery vehicles, the aqueous compositions of the present invention can be modified through the incorporation of a suitable pharmaceutical medicament or diagnostic compound in a concentration ranging from approximately 0.0001% to 50% by weight. As those skilled in the art will appreciate, when compatible medicaments and/or diagnostic compounds are incorporated into the aqueous compositions of the present invention, the drugs will also be incorporated into the gelling matrix following delivery to the target site. As a result, the drug containing viscoelastic gel will reside at the applied location, thereby prolonging the retention and delivery of the incorporated drug. Similarly, fine suspensions of solid drug compositions or particulate drug containing delivery systems may also be incorporated into the reversibly gelling compositions of the present invention. Injection into subcutaneous drug delivery depots or topical delivery by drop instillation of the solutions will then position such delivery systems at the site of choice for sustained bioavailability. This enhanced bioavailability and improved duration of action may lead to overall lower drug dosages being required with resultant improved side effect profiles.

Modifications to the viscosity ranges, pH ranges and temperatures at which the sol-gel transition takes place can be produced in the compositions of the present invention by varying the polymer concentrations as well as through the incorporation of small amounts of univalent or divalent salt. Typically, the addition of small quantities of salt giving a salt-to-combined polymer ratio up to 0.5 and preferably on the order of 0.045 to 0.075 will decrease the viscosity of the composition in the ungelled state if desired. Alternatively, it is contemplated as being within the scope of the present invention to incorporate up to approximately 0.2% to 0.9% by weight salt.

Further objects and advantages of the reversibly gelling compositions of the present invention, as well as a better understanding thereof, will be afforded to those skilled in the art from a consideration of the following detailed explanation of preferred exemplary embodiments thereof. Reference will be made to the appended sheets of drawings which will now be first described briefly.

DETAILED DESCRIPTION OF PREFERRED EMBODIMENTS

Figure 1:
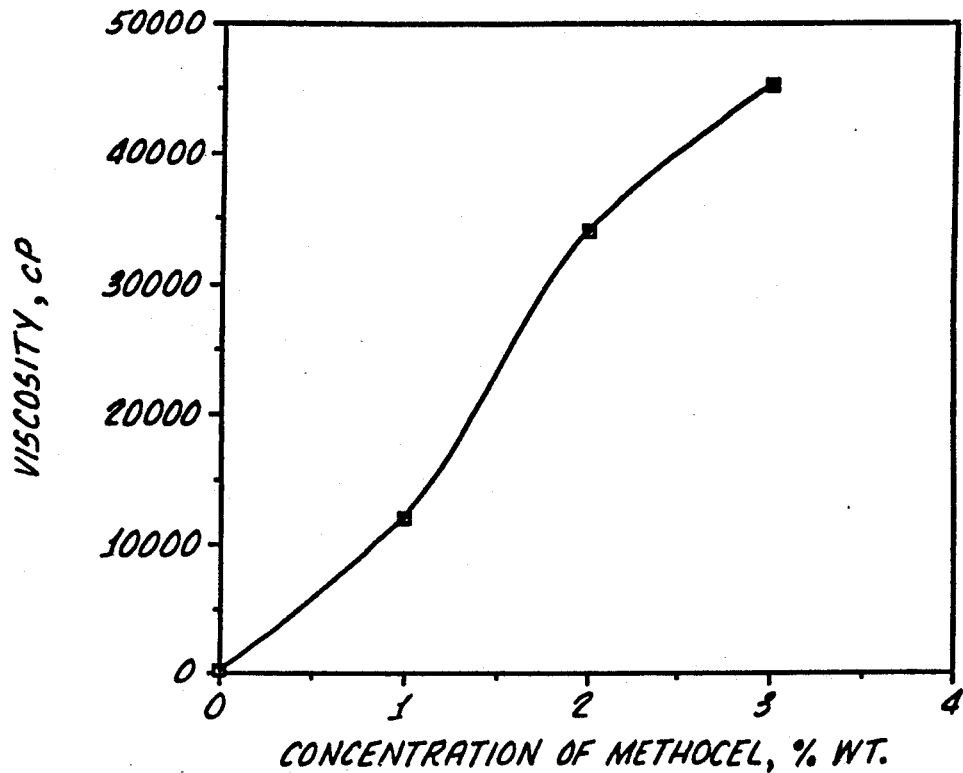
FIG. 1 is a graphical illustration showing the viscosity of a Methocel/Carbopol (Carbopol concentration fixed at 0.3% by weight) mixture as a function of the concentration of a Methocel at room temperature and pH 4.0 Carbopol.

The reversibly gelling aqueous compositions of the present invention are primarily intended for use as drop instillable, oral and injectable drug delivery vehicles as well as for topically applied lubricants, wetting agents and cleaning agents. Accordingly, the preferred exemplary embodiments of the present invention exhibit good, usable flow characteristics at room temperature, yet rapidly gel to highly viscoelastic compounds exhibiting viscosities several orders of magnitude greater at physiological temperatures and pH. Thus, the preferred exemplary embodiments exhibit significant increases in viscosity in response to substantially simultaneous upshifts in both temperature and pH to those conditions encountered in the ocular milieu or at typical injectable drug delivery sites. However, those skilled in the art will appreciate that alternative compositions which gel in response to simultaneous increases in temperature and decreases in pH or the converse may also be produced in accordance with the teachings of the present invention where desired. Similarly, alternative compositions which gel at temperatures significantly above or below those encountered in physiological systems or which exhibit markedly different viscosities relative to those of the preferred embodiments may also be produced. Thus, for purposes of explanation and without limiting the scope of the present invention, the following exemplary embodiments will be discussed in the context of drop instillable or injectable reversibly gelling compounds intended for use in physiological systems.

As those skilled in the art will also appreciate, in addition to responding to changes in both temperature and pH, the ability to produce dramatic changes in viscosity with very small polymer concentrations is a significant feature of the present invention which overcomes many of the disadvantages associated with prior art compositions. For example, the polymer concentrations utilized in accordance with the teachings of the present invention significantly reduce the buffering capacity of the aqueous compositions so produced, thereby effectively eliminating the irritation associated with high buffering capacity compounds such as the pH triggered gelling compositions of the prior art. Similarly, reducing the polymer concentration also reduces the thermal energy requirement of the reversibly gelling compositions and, as a result, the compositions of the present invention gel almost instantaneously upon application. This instantaneous gelation further reduces migration and loss of the compositions of the present invention over the prior art compounds. As an additional benefit, the low polymer concentration compositions of the present invention produce transparent, colorless gels, making them particularly well suited for use as ocular drug delivery vehicles.

In its broadest capacity, an exemplary embodiment of the aqueous compositions of the present invention which exhibits reversible gelation in response to simultaneous variations in both temperature and pH over predetermined ranges comprises an aqueous solution incorporating a stable combination or admixture of at least one thermally-sensitive gelling polymer and at least one pH-sensitive gelling polymer in sufficient amounts to effectively produce reversible gelation over the desired temperature and pH ranges. Preferred thermally-sensitive gelling polymers include alkyl cellulose, hydroxyalkyl cellulose, cellulosic ethers, Pluronic ® polymers and Tetronic ® polymers, with methylcellulose being particularly preferred. Preferred pH-sensitive gelling polymers which increase viscosity with increasing pH are selected from the family of linear, branched or crosslinked acidic polymers such as those containing carboxyl groups, particularly carboxy vinyl polymers of monomers such as acrylates, methacrylic acid, ethacrylic acid, $\beta$-methylacrylic acid, cis-$\alpha$-methylcrotonic acid, trans-$\alpha$-methylcrotonic acid, $\alpha$-butylcrotonic acid, $\alpha$-phenylacrylic acid, $\alpha$-benzylacrylic acid, $\alpha$-cyclohexylacrylic acid, and the like. Exemplary concentrations giving the widest range of viscosities and sol-gel transition temperatures range from approximately 0.1% to 40% by weight thermally-sensitive gelling polymer and from approximately 0.01% to 10% by weight pH-sensitive gelling polymer. For physiological systems, the preferred exemplary concentrations giving the preferred sol-gel transition temperatures and associated viscosities range from approximately 0.1% to 5% by weight thermally-sensitive gelling polymer, and from approximately 0.01% to 0.5% by weight pH-sensitive gelling polymer.

Thus, an exemplary composition of the present invention comprises a homogeneous association complex of a macromolecular mixture of methylcellulose, a polysaccharide available from Dow Chemical under the trade name Methocel, and a cross-linked polyacrylic acid such as Carbopol 940, a hydrophilic acrylic polymer available from the B. F. Goodrich Company. Methocel consists of cellulose chains with a moderate to high degree of hydrophobic methyl group substitution, while Carbopol is a hydrophilic acrylic polymer. When these polymers are mixed in the preferred exemplary aqueous concentrations ranging from 0.1% to 10% by weight Carbopol and from 0.01% to 30% by weight Methocel, a stable combination of the aqueous polymer mixture is formed. This is in direct contrast to the teachings of the prior art wherein aqueous polymer mixtures are extremely difficult, if not impossible, to form due to molecular interaction and precipitation. More importantly, by varying the concentration ranges of this aqueous composition, a wide variety of viscosities and sol-gel transition temperatures and pHs can be produced.

For example, at formation conditions, the pH of the composition will generally range from approximately 2.5 to 6.5, with a preferable range of 4.0 to 5.5. The osmolality will generally range from 20 to 500, with a preferable range between approximately 50 to 400. The osmolality can be adjusted through the addition of physiologically acceptable salts and non-ionic additives such as sodium chloride, potassium chloride, calcium chloride, magnesium chloride, sodium lactate, magnesium phosphate, mannitol, sucrose and glycerine. However, sodium chloride is the preferred tonicity adjuster. More significantly, at temperatures ranging from 0° C. to 45° C., and preferably between 15° C. to 30° C., the viscosity of the composition can be adjusted to range from 20 to 40,000 cP (measured at a shear rate of 2.6 sec$^{-1}$), with a preferred range between 100 to 30,000 cP to produce a drop instillable or injectable viscous fluid. Taking these same formulations and exposing them to physiological conditions of pH approximately 7.4 and temperature approximately 37° C. results in viscosities ranging from 200 to 1 million cP with preferable ranges between approximately 50,000 to 400,000 cP. As a result, the compositions of the present invention can be tailored to produce drop instillable ocular wetting agents, cleaning agents or drug delivery systems which will remain in the eye from fractions of an hour up to ten hours or more, and preferably from two to six hours.

More specifically, when mixed in the exemplary aqueous concentrations of approximately 1% to 3% by weight methylcellulose and 0.2% to 0.4% by weight Carbopol, a stable combination of the aqueous polymer mixture is formed which exhibits a viscosity on the order of 10,000 cP at room temperature (25° C.) and at a pH of between 3.0 and 5.0. When this composition is subjected to physiological temperatures and pH on the order of 37° C. and pH 7.4 two simultaneous intermolecular conformational changes are believed to occur. First, increased ionization produces unwinding of the coils of the acrylic chain. This is accompanied by the expulsion of the hydrophobic functional components of the methylcellulose chain. As a result, within approximately 60 to 120 seconds a three-dimensional network is formed with a concomitant increase in visco-elasticity of several orders of magnitude to approximately 140,000 cP. As those skilled in the art will appreciate, compatible medicaments, diagnostic compounds and microfine particulate drug delivery vehicles incorporated into the composition will be entrapped in the viscoelastic polymer matrix so produced for sustained release applications where desired.

That such significant increases in viscosity should occur with such low polymer concentrations in response to simultaneous changes in both temperature and pH comes in complete contrast to the teachings of the prior art. As noted above, prior art systems for which high viscosity change is induced by temperature change alone require preparations with high polymer concentrations typically much greater than 10% by weight. What is more, with such high concentrations, the heat transfer limitations of the preparations themselves may result in relatively slow or incomplete viscosity increases. Moreover, the high polymer concentrations of the prior art may cause discomfort, polymer crusting on the eyelids, vision blurring, and altered anatomical conditions such as blockage of the lacrimal duct. Similarly, systems for which viscosity change is induced by pH changes alone typically require high polymer concentrations. These pH-triggered systems exhibit a significantly greater buffering capacity than the thermally-triggered systems. In the ocular milieu this high buffering capacity may lead to incomplete gelation and local irritation. Accordingly, the compositions of the present invention are significantly advantageous over these known systems in two major ways. First, for use in physiological conditions, the compositions of the present invention can have significantly less total polymer content; and, second, these compositions effectively utilize both the buffering and heat capacity of the ocular milieu to rapidly and completely induce conformational changes leading to substantially higher viscosity.

As with the compositions of the present invention in general, the rheological properties of the exemplary aqueous solutions of thermally-sensitive methylcellulose and pH-sensitive polyacrylate are effected by the molecular weights of the respective polymers, their concentration, temperature, pH and the presence of other solutes. However, it should be emphasized that the properties of the aqueous compositions of the present invention are uniquely and unexpectedly synergistic. For example, because methylcellulose is non-ionic, in solution alone it is visco-elastically stable over a wide range of pH from approximately 3 to 11. The viscosity of polyacrylate solutions alone is proportional to the polymer concentration, both at lower and higher pH. For example, at polymer concentrations between 0.1% and 0.4% by weight, aqueous polyacrylate solutions are very inviscid over a pH range of 3 to 7. Additionally, aqueous solutions containing more than 0.5% by weight polyacrylate have a much higher buffer capacity and need additional neutralizing base to increase their viscosity. However, mixtures of such pH-sensitive and thermally-sensitive polymers in accordance with the teachings of the present invention exhibit viscosities which are substantially in excess of the sum of the individual viscosities of the individual aqueous polymer solutions at both lower and higher pH. For example, at pH 4.0, the viscosity of a 3% by weight methylcellulose solution measured with a Carri-Med rheometer at a shear rate of approximately 2.6 sec$^{-1}$ is approximately 18,000 cP. Similarly, the viscosity of a 0.2% Carbopol solution at pH 4.0 is approximately 50 cP. The viscosity of the mixture of these 2 polymers produced in accordance dance with the teachings of the present invention at pH 4.0 is approximately 30,000 cP. As those skilled in the art will appreciate, 30,000 cP is substantially greater than the anticipated combined viscosity of 18,050 cP.

The following table is an illustrative listing of the rheological properties that can be expected with the aqueous compositions of the present invention utilizing an exemplary formulation of Methocel A4M methylcellulose and Carbopol (940), a crosslinked polyacrylate.

TABLE 1

| Viscosity for Typical Methocel (1% by Weight)/Carbopol (0.3% by Weight) Preparation | | | | |
|---|---|---|---|---|
| Temperature | 25° C. | | 37° C. | |
| pH | 4.0 | 7.4 | 4.0 | 7.4 |
| Viscosity, cP | 11,500 | 90,800 | 20,000 | 140,000 |
| (shear rate approximately 2.6 sec$^{-1}$) | | | | |

Figure 2:
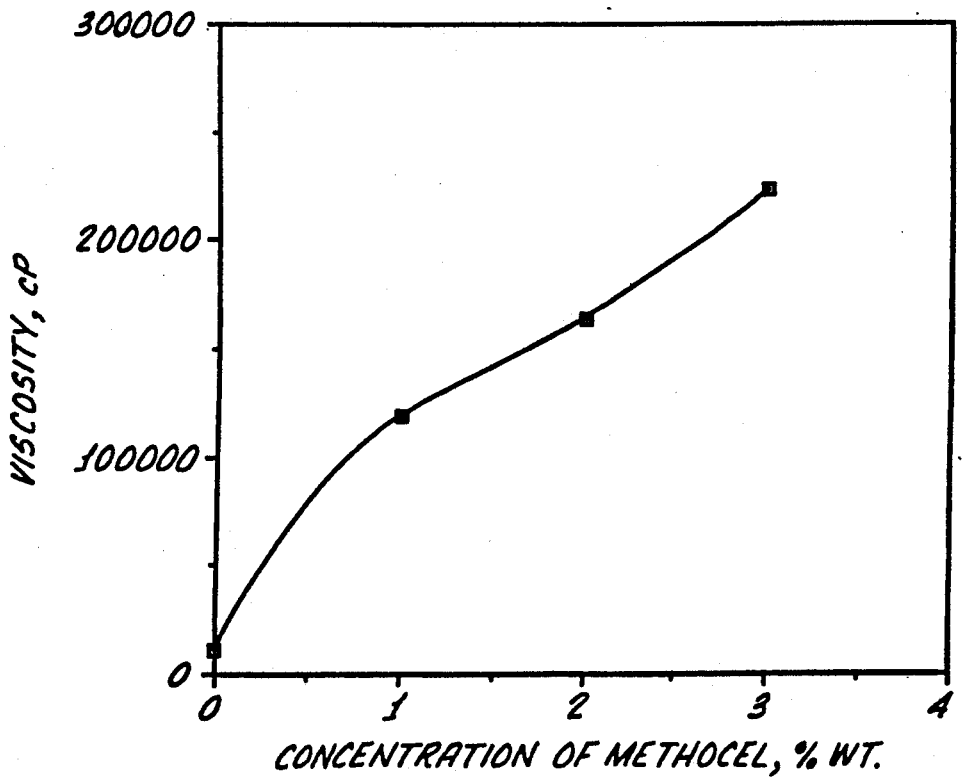
FIG. 2 is a graphical illustration showing the viscosity of a Methocel/Carbopol (Carbopol concentration fixed at 0.3% by weight) mixture as a function of the concentration of a Methocel at 37° C. and pH 7.4 Carbopol.

FIGS. 1 and 2 more clearly show the rheologic properties of exemplary Methocel/Carbopol mixtures in accordance with the teachings of the present invention. As shown in FIGS. 1 and 2, the viscosity of an exemplary aqueous Methocel/Carbopol composition is plotted as a function of the concentration of Methocel (the Carbopol concentration being fixed at 0.3% by weight) at room temperature and pH 4 in FIG. 1 and at 37° C. and pH 7.4 in FIG. 2. As shown in FIG. 1, aqueous compositions exhibiting a viscosity ranging from approximately 20 to in excess of 40, 000 cP can be produced at room temperature and pH 4 which, as shown in FIG. 2, gel to viscosities ranging from approximately 200 to well in excess of 200,000 at physiological conditions. As those skilled in the art will also appreciate, the foregoing temperature and pH conditions discussed in Table 1 are exemplary of those present at room temperature (25° C.) and in the ocular milieu where the cul-de-sac of the eye is bathed with isotonic lacrimal fluid at pH 7.4 and approximately 37° C. Thus, it is readily apparent that the exemplary composition disclosed in Table 1 is a freely-flowing viscous liquid at its formulation temperature and pH which, upon contract with tear fluid and physiologic conditions, forms a highly viscoelastic gel.

Additionally, the highly viscoelastic gels formed at the physiologic temperature and pH are transparent with a specific gravity of approximately 1.01 and a refractive index of approximately 1.33. Thus, the aqueous compositions of the present invention can easily be administered to the eye in drop form and will rapidly gel under the combined effect of both temperature and pH when placed in the eye thereby preventing their rapid elimination from the eye through the lacrimal drainage system. Moreover, the favorable optical properties and low polymer concentration of the compositions should cause minimal or no visual perturbation once gelled in situ. It should also be appreciated that these exemplary gelled compositions exhibit a mucoadhesive property which further aids their retention in the cul-de-sac of the eye. Also, the gelled polymers are self-lubricating and relatively soft and deformable which increases patient comfort and acceptability.

Figure 3:
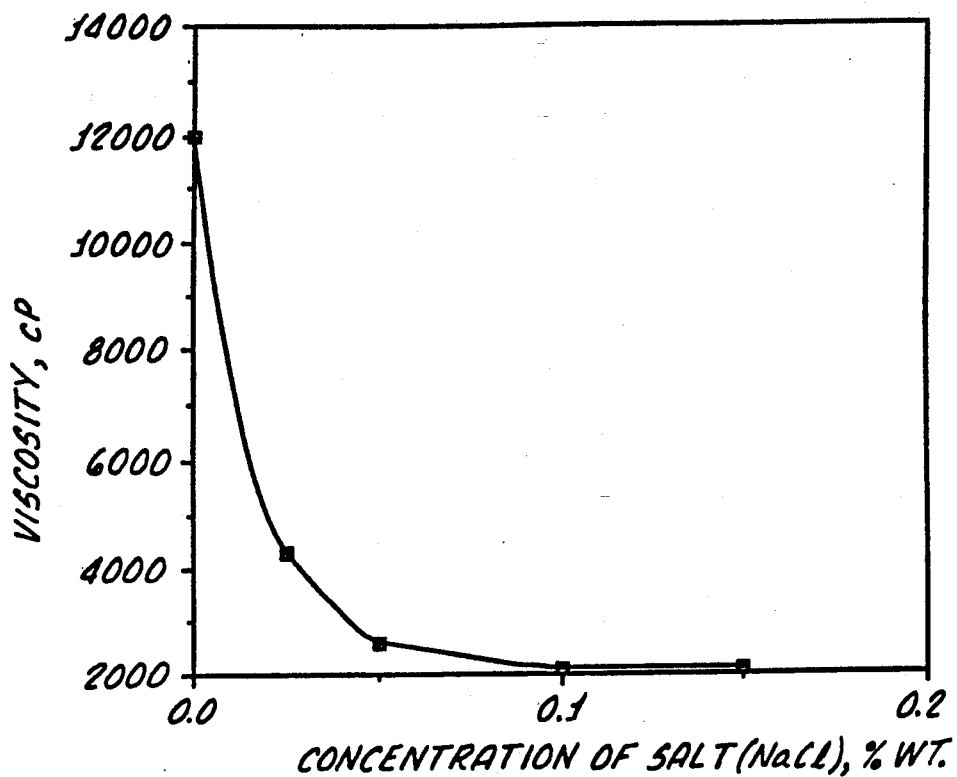
FIG. 3 is a graphical illustration showing the viscosity of a Methocel (1%)/Carbopol (0.3%) mixture as a function of salt concentration at room temperature and pH 4.0.
Figure 4:
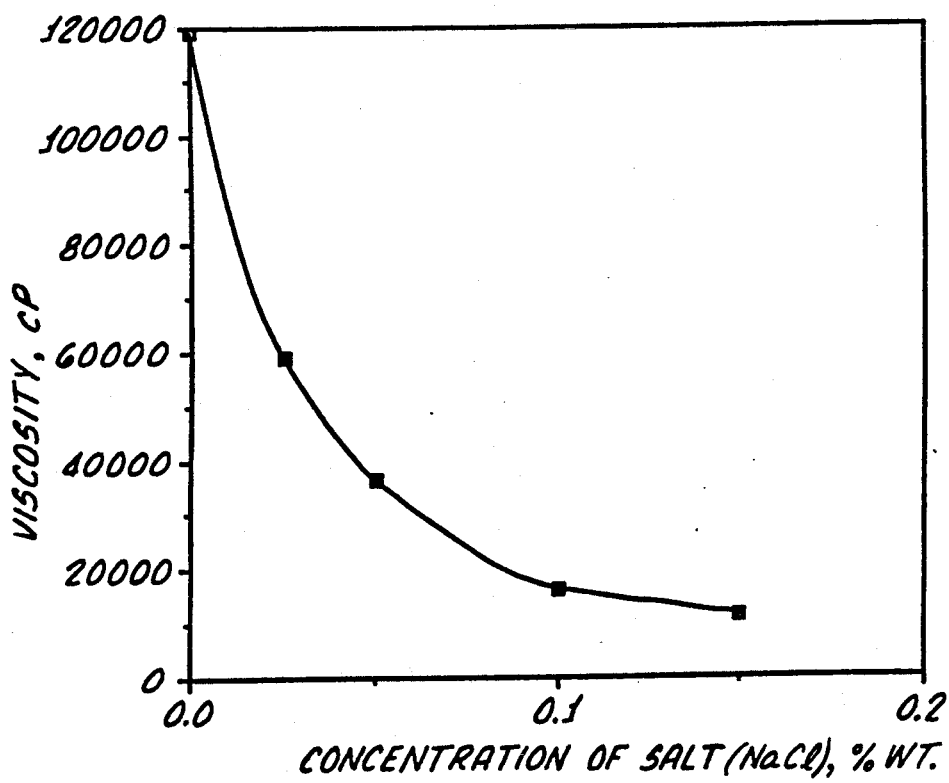
FIG. 4 is a graphical illustration showing the viscosity of a Methocel (1%)/Carbopol (0.3%) mixture as a function of salt concentration at 37° C. and pH 7.4.

As shown in FIGS. 3 and 4, it should also be noted that the viscosity of the aqueous compositions of the present invention can be modified by adding a pharmaceutically acceptable salt such as mono- or divalent salts including sodium chloride, potassium chloride, calcium chloride or mixtures thereof, as well as suitable alkali metal salts such as sodium sulfate and the like. Preferred salt to total polymer ratios will range from 0 to approximately 0.5 and preferably from approximately 0.045 to 0.075. As shown in FIGS. 3 and 4, the addition of salt exhibits its most significant relative effect on the lower viscosity of the aqueous system. For example, slight increases in the salt concentration apparently preferentially decrease the lower viscosity ranges while exhibiting a comparatively minor decrease on the upper viscosity ranges.

Figure 5:
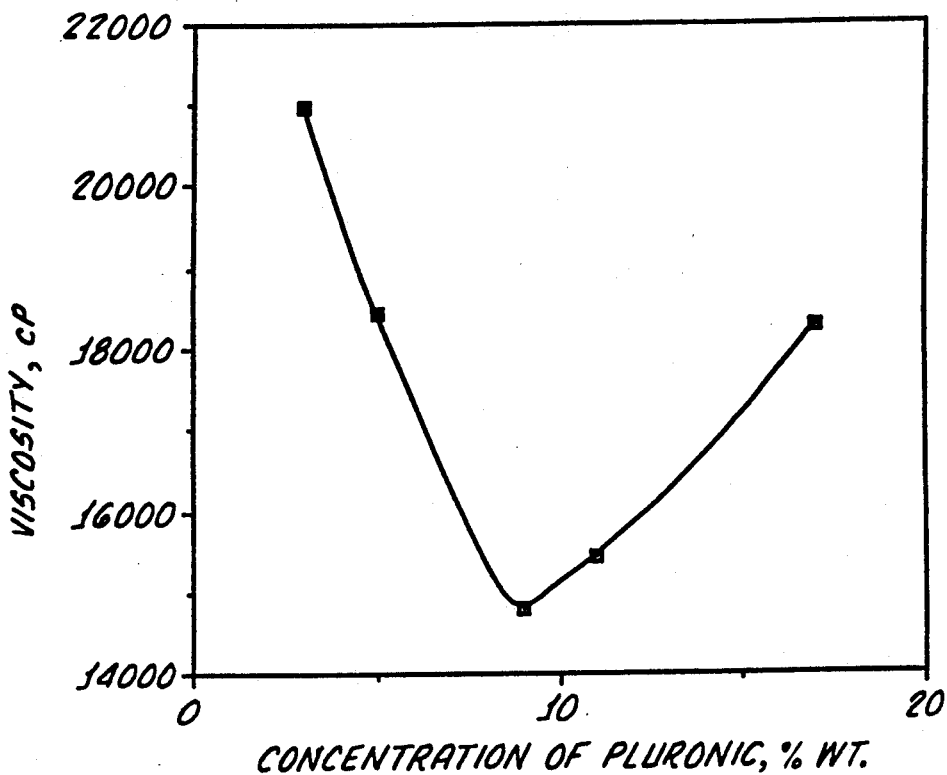
FIG. 5 is a graphical illustration showing the viscosity of a Pluronic ®/Carbopol (Carbopol concentration fixed at 0.3% by weight) mixture as a function of the concentration of Pluronic ® at room temperature and pH 5.0 Carbopol.
Figure 6:
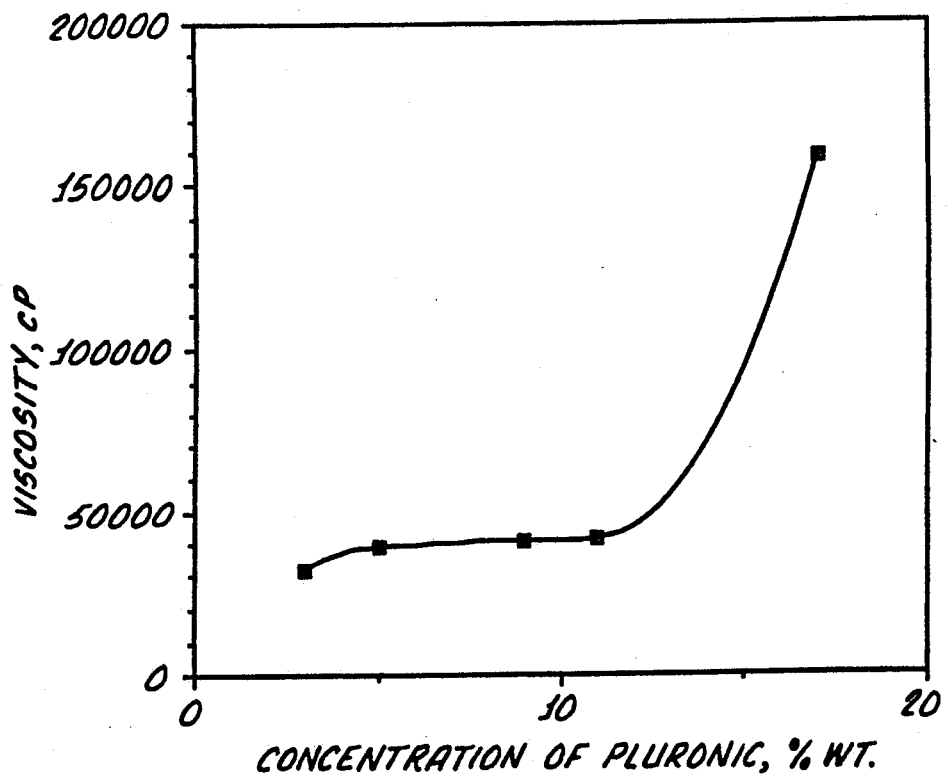
FIG. 6 is a graphical illustration showing the viscosity of a Pluronic ®/Carbopol (Carbopol concentration fixed at 0.3% by weight) mixture as a function of the concentration of Pluronic ® at 37° C. and pH 7.4 Carbopol.

The rheological properties of alternative exemplary compositions produced in accordance with the teachings of the present invention are illustrated in FIGS. 5 through 8. FIGS. 5 and 6 illustrate the viscosity of a Pluronic ®/Carbopol mixture prepared in accordance with the teachings of the present invention. Pluronic ® polymers are block copolymers of propylene oxide and ethylene oxide and are thermally-sensitive gelling polymers. It is contemplated as being within the scope of the present invention to form reversibly gelling aqueous compositions comprising stable mixtures of from 0.01% to 10% by weight pH-sensitive gelling polymers such as Carbopol, and from approximately 1% to 30% by weight Pluronic ® polymer. As shown in FIGS. 5 and 6, such mixtures form viscous liquids at room temperature and pH 5 and rapidly gel to highly viscoelastic gels at physiologic conditions.

Figure 7:
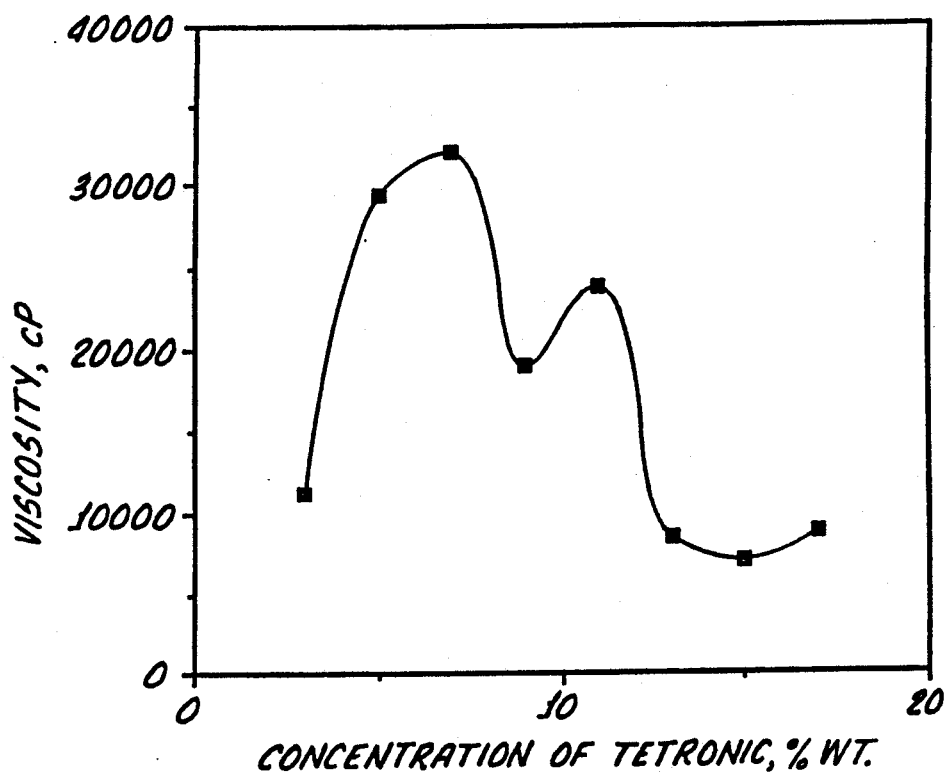
FIG. 7 is a graphical illustration showing the viscosity of a Tetronic ®/Carbopol (Carbopol concentration fixed at 0.3% by weight) mixture as a function of the Tetronic ® concentration at room temperature and pH 5.0 Carbopol.
Figure 8:
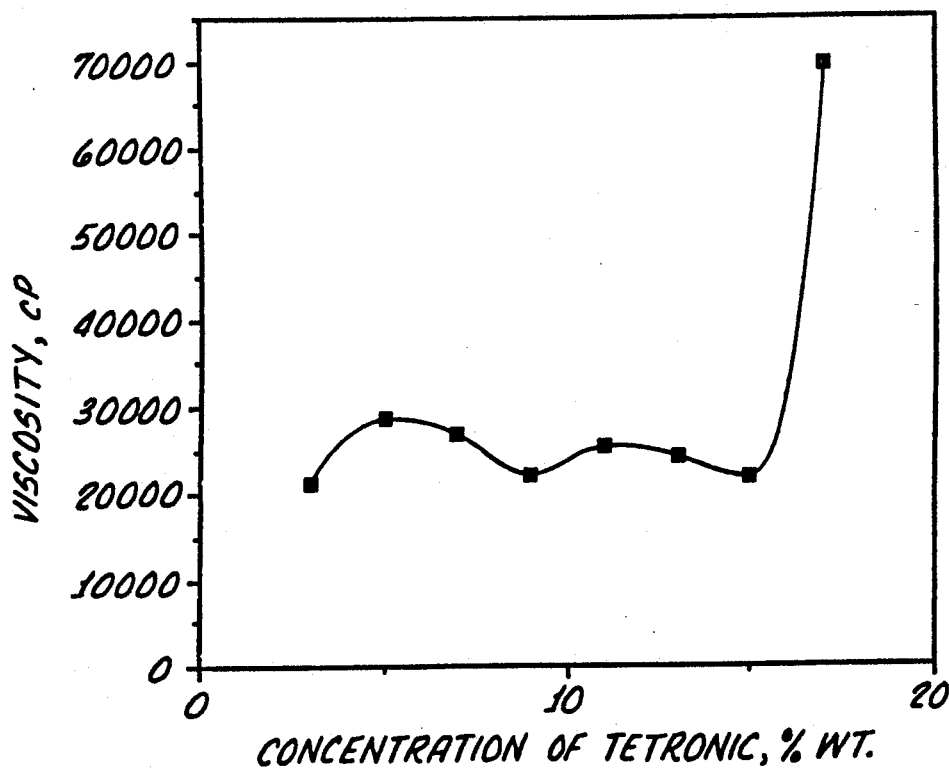
FIG. 8 is a graphical illustration showing the viscosity of a Tetronic ®/Carbopol (Carbopol concentration fixed at 0.3% by weight) mixture as a function of the Tetronic ® concentration at 37° C. and pH 7.4 Carbopol.

Similarly, alternative compositions can be formulated within the scope of the present invention utilizing Tetronic ® polymers. Tetronic ® polymers are tetrafunctional block copolymers derived from the sequential addition of propylene oxide and ethylene oxide to ethylenediamine. As shown in FIGS. 7 and 8, reversibly gelling aqueous compositions produced in accordance with the teachings of the present invention utilizing Tetronic ® polymers can also be formulated to remain liquid at room temperature and lower pHs on the order of 4.0 to 5.5 while gelling to highly viscoelastic gels at physiological conditions. It should be noted that these alternative polymer compositions extend the temperature ranges available for gelling and formulation without significantly modifying the pH and osmolality conditions associated with these compositions.

Though the foregoing exemplary compositions all reversibly gel in response to simultaneous upshifts in both temperature and pH, it is also possible to utilize the teachings of the present invention to produce aqueous compositions which are liquid at higher pH and lower temperatures and gel at lower pH (neutral or lower) and higher temperatures. For example, polymers containing weakly basic pendant groups such as amine containing polymers of poly-N,N dimethylaminoethyl methacrylate can be combined with methylcellulose, Pluronic ® or Tetronic ® polymers or combinations thereof. Such combinations will be liquid at higher pH and lower temperature while gelling at lower pH and higher temperature.

As those skilled in the art will appreciate, the aqueous compositions of the present invention may be utilized as wetting agents or lubricants for contact lenses or the treatment of conditions such as dry eye. However, it is preferred that the compositions be utilized as drug delivery vehicles for administering a variety of pharmaceutical medicaments and diagnostic compounds.

The most promising drugs for incorporating into the aqueous drug delivery compositions of the present invention are levobunolol, pilocarpine, dipivefrin and others which exhibit poor bioavailability. Other exemplary drugs or diagnostic agents which can be administered by the aqueous compositions of the present invention include, but are not limited to:

(1) antibacterial substances such as beta-lactam antibiotics, such as cefoxitin, n-formamidoyl-thienamycin and other thienamycin derivatives, tetracyclines, chloramphenicol, neomycin, carbenicillin, colistin, penicillin G, polymyxin B, vancomycin, cefazolin, cephaloridine, chibrorifamycin, gramicidin, bacitracin, sulfonamides; aminoglycoside antibiotics such as gentamycin, kanamycin, amikacin, sisomicin and tobramycin; nalidixic acid and analogs such as norfloxacin and the antimicrobial combination of flucalanine/pentizidone; nitrofurazones, and the like;

(2) antihistaminics and decongestants such as pyrilamine, chlorpheniramine, tetrahydrazoline, antazonline, and the like;

(3) anti-inflammatorics such as cortisone, hydrocortisone, hydrocortisone acetate, betamethasone, dexamethasone, dexamethasone sodium phosphate, preunisone, methylpredinisolone, medrysone, fluorometholone, fluocortolone, preunisolone, preunisolone sodium phosphate, triamcinolone, indomethacin, sulindac, its salts and its corresponding sulfide, and the like;

(4) miotics and anticholinergics such as echothiophate, pilocarpine, physostigmine salicylate, diisopropylfluorophosphate, epinephrine, dipivolyl epinephraine, neostigmine, echothiophate iodide, demecarium bromide, carbachol, methacholine, bethanechol, and the like;

(5) mydriatics such as atropine, homatropine, scopolamine, hydroxyamphetamine, ephedrine, cocaine, tropicamide, phenylephrine, cyclopentolate, oxyphenonium, eucatropine, and the like; and other medicaments used in the treatment of eye conditions or diseases such as (6) antiglaucoma drugs, for example, betaxalol, pilocarpine, timolol, especially as the maleate salt and R-timolol and a combination of timolol or R-timolol with pilocarpine. Also included are epinephrine and epinephrine complex or prodrugs such as the bitartrate, borate, hydrochloride and dipivefrin derivatives and hyperosmotic agents such as glycerol, mannitol and urea;

(7) antiparasitic compounds and/or anti-protozoal compounds such as ivermectin; pyrimethamine, trisulfapyrimidine, clindamycin and corticosteroid preparations;

(8) antiviral effective compounds such as acyclovir, 5-iodo-2'-deoxyuridine (IDU), adenosine arabinoside (Ara-A), trifluorothymidine, and interferon and interferon inducing agents such as Poly I:C;

(9) carbonic anhydrase inhibitors such as acetazolamide, dichlorphenamide, 2-(p-hydroxyphenyl)thio-5-thiophenesulfonamide, 6-hydroxy-2-benzothiazolesulfonamide and 6-pivaloyloxy-2-benzothiazolesulfonamide;

(10) anti-fungal agents such as amphotericin B, nystatin, flucytosine, natamycin, and miconazole;

(11) anesthetic agents such as etidocaine cocaine, henoxinate, dibucaine hydrochloride, dyclonine hydrochloride, naepaine, phenacaine hydrochloride, piperocaine, proparacaine hydrochloride, tetracaine hydrochloride, hexylcaine, bupivacaine, lidocaine, mepivacaine and prilocaine;

(12) ophthalmic diagnostic agents such as
(a) those used to examine the retina and chloride-sodium fluorescein;
(b) those used to examine the conjunctive, cornea and lacrimal apparatus such as fluorescein and rose bengal; and
(c) those used to examine abnormal pupillary responses such as methacholine, cocaine, adrenaline, atropine, hydroxyamphetamine and pilocarpine;

(13) ophthalmic agents used as adjuncts in surgery such as alphachymotrypsin and hyaluronidase;

(14) chelating agents such as ethylenediamine tetraacetate (EDTA) and deferoxamine;

(15) immunosuppressive agents and anti-metabolites such as methotrexate, cyclophosphamide, 6-mercaptopurine, and azathioprine;

(16) peptides and proteins such as atrial natriuretic factor, calcitonin-gene related factor, lutinizing hormone, releasing hormone, neuroterisin, vasoactive intestinal peptide, vasopressin, cyclosporine, interferon, substance P enkephalins, epidermal growth factor, eyederived growth factor, fibronectin, insulin-like growth factor and mesodermal growth factor;

(17) lubricating agents such as sodium hyaluronate or polyvinyl alcohol; and

(18) combinations of the above such as antibiotic/anti-inflammatory as in neomycin sulfate-dexamethasone sodium phosphate, concomittant anti-glaucoma therapy such as timolol maleate-aceclidine.

As those skilled in the art will appreciate, the foregoing listing of pharmaceutical compounds is exemplary only. Because the drug delivery compositions of the present invention are uniquely suited for utilization in a wide variety of physiological applications such as the ocular, oral, nasal, rectal or subcutaneous administration of pharmaceutical compounds, a wide variety of pharmaceutical agents may be incorporated therein. Accordingly, the foregoing listing of pharmaceutical agents is not intended to limit the scope of the present invention and is exemplary only.

Preferably, when utilized as an aqueous drug delivery vehicle for drop instillation, oral administration or injection, the compositions of the present invention can be modified to include from approximately 0.0001% to 50% by weight pharmaceutical medicament or diagnostic agent. To prepare an aqueous drug delivery vehicle in accordance with the teachings of the present invention, an appropriately effective amount of the pharmaceutical compound of choice is simply incorporated into the aqueous composition at the composition formulation temperatures and pHs. Preferably, the compound of choice will be soluble in the solution or will be homogeneously dispersed and will not react with the polymer system. Soluble pharmaceutical compounds will readily dissolve in the aqueous composition, whereas insoluble compounds will preferably be particularized for even dispersion throughout the compositions. Along these lines, it is also contemplated as being within the scope of the present invention to incorporate insoluble or erodible microparticulate drug delivery systems such as those known in the art into the aqueous compositions. In this manner, controlled release drug delivery systems can be incorporated into the aqueous compositions of the present invention and retained in position when administered by drop or injection.

Following gelation, the medicament or diagnostic agent will be incorporated into the gelled polymer matrix and will remain on site for sustained drug delivery as the solidified gel slowly erodes and the incorporated pharmaceutical agent diffuses out into the surrounding lacrimal or physiological fluid. Additionally, it should be noted that by varying the concentration of pharmaceutical compound within the aqueous composition, it is possible to modify and control the quantity of pharmaceutical compound delivered by drop or injection. For example, a liquid drug delivery vehicle can be prepared in accordance with the teachings of the present invention containing from about 0.01 to about 5% of the medicament or pharmaceutical agent of choice on a weight to weight basis. For drop instillation methodologies the drop size will preferably range from approximately 20 $\mu$l to 50 $\mu$l, with 25 $\mu$l drops being particularly preferred. Thus, from one drop of the liquid composition which contains about 25 $\mu$l of solution, one would obtain about 0.0025 mg to about 1.25 mg of drug.

The following non-limiting examples are offered as being illustrative of the properties of exemplary compositions of the present invention. In the following example, concentrations are expressed in weight percent (% w/w), deionized water is utilized to make the formulations, and the formulation temperatures are 25° C.

EXAMPLE I

Thirty gm of water was heated to about 90° C. To this heated water, 3 gm of Methocel A4M (available from Dow Chemicals, Midland, Mich.) was added and the mixture was stirred until the polymer particles were thoroughly wetted and evenly dispersed. Sixty-seven gm cold water was added to lower the temperature of the dispersion to about 10° C. for complete solubilization. The final mixture was brought to 100 gm of total weight by adding deionized water to give 3% w/w of Methocel mixture. The resultant mixture was stirred for two hours at 2.5 rpm.

In a separate container, 0.9 gm of Carboxypolymethylene (available from B. F. Goodrich, Cleveland, Ohio, as Carbopol 940) was completely dispersed and stirred in 90 gm of deionized water. The mixture was agitated at 100 rpm for two hours following which water was added to bring the final mixture weight to 100 gm and 0.9% w/w of Carbopol content.

A physical admixture of 20 gm of the 3% w/w of Methocel solution (prepared as mentioned above) and 20 gm of the 0.9% w/w Carbopol solution was prepared. 0.06 gm of Levobunolol was dissolved in 18 gm of deionized water and added to the physical admixture of the polymers. The resultant drug containing aqueous solution was then titrated with 5N NAOH to pH 4.5 following which the final formulation was brought to 60 gm by adding deionized water. The resultant formulation was as follows: 1% Methocel, 0.3% Carbopol and 0.1% Levobunolol. The viscosity was measured using a Carri-Med Rheometer and a rheogram depicting shear stress v/s shear rate was obtained. The formulation had a viscosity of 12,000 cP at a shear rate of 2.64/sec. The mixture was a smooth flowing liquid having droppable characteristics.

EXAMPLE II

Methocel A4M mixture, 3% w/w, was prepared as set forth under Example I. Forty grams of this solution was blended with 0.12 gm of Carbopol 940, 0.6 gm of Levobunolol and 18 gm of deionized water. The mixture was then stirred at 50 rpm at room temperature for 15 hours. The resultant drug containing mixture was titrated with 5N NAOH to pH 4.2 following which deionized water was added to bring the final formulation weight to 100% (60 gm) followed by stirring at 50 rpm for another two hours. The final formulation obtained was as follows: 2% Methocel, 0.2% Carbopol and 0.1% Levobunolol. The viscosity was measured using a Carri-Med Rheometer and a rheogram depicting shear stress v/s shear rate was obtained. The formulation had a viscosity of 806 cP at a shear rate of 2.64/sec. The mixture was a smooth flowing liquid having droppable characteristics.

EXAMPLE III

Methocel A4M mixture, 3% w/w, was prepared as set forth under Example I. A preblend of 0.06 gm of salt (Sodium Chloride) and 0.06 gm of Levobunolol was prepared. Forty gm of Methocel solution was blended with 0.18 gm of Carbopol 940, the preblend of salt and Levobunolol and 16 gm of water. The mixture was then stirred at 50 rpm for 15 hours and then titrated with 5N NAOH to pH 4. 00. The final formulation was brought to 100% weight (60 gm) by adding deionized water and stirred at 50 rpm for another two hours. The final formulation obtained was as follows: 2% Methocel, 0.3% Carbopol, 0.1% Sodium Chloride and 0.1% Levobunolol. The viscosity was measured using a Carri-Med Rheometer and a rheogram depicting shear stress v/s shear rate was obtained. The formulation had a viscosity of 8317 cP at a shear rate of 2.65/sec. The mixture was a smooth flowing liquid having droppable characteristics.

EXAMPLE IV

Methocel A4M mixture, 3% w/w, was prepared as set forth under Example I. A preblend of 0. 06 gm of Levobunolol and 0. 18 gm of Carbopol 940 was prepared. A physical admixture of 20 gm of the 3% w/w of Methocel solution and the preblend was prepared, followed by adding 38 gm of deionized water. The mixture was stirred for 15 hours at 50 rpm to assure complete mixing. The resultant drug containing aqueous solution was then titrated with 5N NAOH to pH 4.12 following which the final formulation was brought to 60 gm by adding deionized water followed by mixing for two hours at 50 rpm. The resultant formulation was as follows: 1% Methocel, 0.3% Carbopol and 0.1% Levobunolol. The viscosity of the formulation was measured using a Carri-Med Rheometer and a rheogram depicting shear stress v/s shear rate was obtained. The formulation had a viscosity of 3154 cP at a shear rate of 2.55/sec. The mixture was a smooth flowing liquid having droppable characteristics.

EXAMPLE V

Thirty gm of water was heated to 90° C. To this heated water, 5 gm of Methocel A4M (available from Dow Chemicals, Midland, Mich.) was added and the mixture was stirred until the polymer particles were thoroughly wetted and evenly dispersed. The remainder of the water, 67 gm, was added as cold water to lower the temperature of dispersion to about 10° C. for complete solubilization. The final mixture was brought to 100 gm of total weight by adding purified water to give 5% W/w of Methocel mixture. The resultant mixture was stirred for two hours at 25 rpm.

Twenty grams of deionized water was measured and to this 0.12 gm of Carbopol 940 (available from B. F. Goodrich) was added. The solution was stirred at 50 rpm for two hours until all the Carbopol was dispersed into the solution. Thirty-six grams of 5% Methocel solution, as prepared above, was added to the Carbopol solution followed by the addition of 0.09 gm of Sodium Chloride. The physical admixture was stirred for 12 hours at 50 rpm to ensure complete mixing and dispersion of the polymers. The mixture was then titrated with 5N NAOH to pH 3.53 following which the final formulation was brought to 100% weight. The final formulation by weight percent was: 3% Methocel, 0.2% Carbopol, 0.15% Sodium Chloride. The viscosity of the formulation was measured using a Carri-Med Rheometer and a rheogram depicting shear stress v/s shear rate was obtained. The formulation had a viscosity of 16,610 cP at a shear rate of 2.64/sc. The mixture was a smooth flowing liquid having droppable characteristics.

EXAMPLE VI

Methocel A4M mixture, 5% w/w, was prepared as set forth under Example V. A preblend of 0.12 gm of Carbopol 940 and 0.14 gm of Sodium Chloride was prepared. This preblend was added to 36 gm of the 5% w/w of Methocel solution followed by the addition of 20 gm of water. The mixture was stirred at 50 rpm for 15 hours and then titrated with 5N NAOH to pH 3.5. The final formulation was then brought to 100% weight by adding deionized water and further stirred for two hours at 50 rpm. The final formulation by weight percent was: 3% Methocel, 0.2% Carbopol, 0.25% Sodium Chloride. The viscosity was measured using a Carri-Med Rheometer and a rheogram depicting shear stress v/s shear rate was obtained. The formulation had a viscosity of 16,600 cP at a shear rate of 2.85/sec. The mixture was a smooth flowing liquid having droppable characteristics.

EXAMPLE VII

Methocel A4M mixture, 3% w/w, was prepared as set forth under Example I. Carbopol 940 (available from B. F. Goodrich), 0.12 gm, was dispersed in 18 gm of deionized water. After complete dispersion, 0.09 gm of Sodium Chloride was added to this Carbopol solution and the resultant mixture was stirred at 50 rpm for 10 hours. Forty grams of 3% Methocel was then added to the Carbopol/Salt solution and the mixture stirred for four hours. The resultant mixture was then titrated with 5N NAOH to pH 4.49 following which deionized water was added to bring the final formulation to 100% weight (60 gm). The final formulation by weight percent was: 2% Methocel, 0.2% Carbopol, 0.15% Sodium Chloride. The viscosity was measured using a Carri-Med Rheometer and a rheogram depicting shear stress v/s shear rate was obtained. The formulation had a viscosity of about 11,500 cP at a shear rate of 2.64/sec. The mixture was a smooth flowing liquid having droppable characteristics.

EXAMPLE VIII

An exemplary aqueous gel mixture was prepared containing 3% Methocel A4M, 0.3% Carbopol 940 and 0.2% salt with a 1% loading of Acid Orange 8 dye for an in vitro release kinetic study. A 0.4 gram solidified gel sample of this composition was placed in a USP dissolution kettle (paddle speed 50 rpm) containing 500 ml phosphate buffer at pH 7.4 and 37° C. The dissolution time for the gel was observed to be in excess of nine hours. A $T_{50}$ value of approximately 55 minutes and a $T_{90}$ value of approximately 200 minutes was obtained from the dye release profile of the gel.

EXAMPLE IX

An analysis of in vivo gel retention time was undertaken utilizing rabbit eyes. The gel mixture of Example 1 was tagged with high molecular weight FITC dextran (MW approximately 70,000). Gel formation after installation of a 50 microliter drop appeared to be quite rapid and led to the formation of a continuous coating on the pre-corneal surface of the eye by the gel matrix. Photographic and biomicroscopic assessments were obtained over a seven hour observation period. Two significant retention times of the delivery vehicle in the rabbit eye were obtained: (1) a distinct gelatinous formation in the lower cul-de-sac; and (2) a smooth, apparently uniform film over the ocular surface. The distinct gel formation lasted for approximately three hours while the uniform film retention time was 0 to 6.5 hours or more.

EXAMPLE X

Sodium fluorescein was used as a marker with the composition of Example 2 to monitor its penetration into the anterior chamber of the eye. The rabbit eye anterior chamber was monitored using a slit lamp technique and an incremental increase in fluorescence over a period of seven hours after the installation of the gel labelled with fluorescein was observed.

EXAMPLE XI

Probe acute toxicological studies did not reveal any toxicity issues. No irritation, injection, staining or cytotoxicity was observed with the gel mixture in rabbit eyes. Ocular status was noted to be healthy after 24 hours post-installation.

EXAMPLE XII

An exemplary drug delivery vehicle incorporating erodible microparticulate drug delivery vehicles was prepared as follows. Levobunolol was blended into a heated slurry of poly(orthoester) and cooled to solidify the mixture. The drug containing poly(orthoester) was ground to produce microparticulates ranging in size from 1 to 300 μm. These particles were physically dispersed in the exemplary reversible gelling composition of Example I to produce a reversibly gelling drug delivery vehicle incorporating erodible drug containing microparticulates.

EXAMPLE XIII

An exemplary therapeutic agent for the treatment of severe keratoconjunctivitis sicca was produced from an aqueous composition containing 1% by weight Methocel, 0.3% by weight Carbopol 940, and 0.1% by weight sodium hyaluronate and isotonically adjusted with glycerol at pH 4.5 to 5.5. Upon installation of a 50 μl drop in rabbit eyes, almost instantaneous gelation was observed. Examination of the rabbit eyes 24 hours following installation indicated healthy ocular status.

As those skilled in the art will appreciate, though the foregoing examples were primarily directed to ocular drug delivery vehicles, wetting agents and topical compositions, it is contemplated as being within the scope of the present invention to utilize the aqueous compositions of the present invention as drug delivery vehicles which can be orally administered or injected either subcutaneously or intramuscularly. Following injection of the free-flowing drug delivery vehicle, the aqueous composition will rapidly gel to form a stable drug delivery depot from which the incorporated pharmaceutical compound can diffuse.

However, it is preferred that the aqueous compositions of the present invention be utilized to deliver pharmaceutical compounds to the surface of the eye. In this manner, the pharmaceutical compounds can be retained in contact with the eye surface over an extended period of time to enhance the bioavailability of the incorporated pharmaceutical compound. Such a drug delivery method would comprise the steps of preparing the aqueous composition of the present invention containing the above described effective amount of pharmaceutical compound and introducing the composition into the lacrimal secretions of the eye. Once introduced into the cul-de-sac of the eye, the composition will rapidly gel and resist the dilution and depletion normally associated with tear turnover in the eye. The mucoadhesive gel so formed will remain in the eye for significant periods of time, slowly eroding and releasing the dissolved pharmaceutical agent dispersed within it. This prolonged residence time leads to more effective levels of concentration of the pharmaceutical agent in the tear film and may actually result in a decrease in the overall dosage that need be administered.

Having thus described preferred exemplary embodiments of the present invention, it should be noted by those skilled in the art that the disclosures herein are exemplary only and that alternatives, adaptations and modifications may be made within the scope of the present invention. Thus, by way of example and not limitation, it is contemplated that ionic strength sensitive gelling polymers also may be utilized which thicken when exposed to changes in ionic strength. Accordingly, the present invention is not limited to the specific embodiments illustrated herein.

We claim:

1. An aqueous pharmaceutical composition of matter exhibiting the property of reversible gelation in response to substantially simultaneous variations in both temperature and pH over predetermined ranges, said composition comprising:
   an aqueous solution including approximately 0.1% to 30% by weight thermally-sensitive gelling polymer and approximately 0.01% to 10% by weight pH sensitive gelling polymer whereby said aqueous composition exhibits a reversible viscosity change ranging between approximately 200 to 1,000,000 cP in response to substantially simultaneous variations in both temperature and pH over respective ranges between approximately 0° C. to 60° C. and pH 2.5 to pH 7.5.

2. An aqueous pharmaceutical composition of matter exhibiting the property of reversible gelation in response to substantially simultaneous variations in both temperature and pH over predetermined ranges, said composition comprising:
   an aqueous solution including approximately 0.1% to 30% by weight thermally-sensitive gelling polymer and approximately 0.01% to 10% by weight pH sensitive gelling polymer whereby said aqueous composition exhibits a reversible viscosity change ranging between approximately 200 to 1,000,000 cP in response to substantially simultaneous variations in both temperature and pH over respective ranges between approximately 25° C. to 37° C. and pH 4.5 to pH 7.4.

3. The composition of claim 2 wherein said at least one thermally-sensitive gelling polymer is selected from the group consisting of alkylcellulose, hydroxyalkyl cellulose, block copolymers of polyoxyethylene and polyoxypropylene, and tetrafunctional block polymers of polyoxyethylene and polyoxypropylene and ethylenediamine.

4. The composition of claim 2 wherein said at least one thermally-sensitive gelling polymer is methylcellulose.

5. The composition of claim 2 wherein said at least one pH-sensitive gelling polymer is an acidic polymer.

6. The composition of claim 5 wherein said acidic polymer is a carboxyl containing polymer.

7. The composition of claim 6 wherein said carboxyl containing polymer is polyacrylate.

8. The composition of claim 2 wherein said at least one thermally-sensitive gelling polymer is methylcellulose and said at least one pH-sensitive gelling polymer is polyacrylate.

9. The composition of claim 8 wherein said aqueous composition comprises approximately 0.1% to 5% by weight methylcellulose and approximately 0.01% to 10% polyacrylate.

10. The composition of claim 8 wherein said aqueous composition comprises approximately 1% by weight methylcellulose and approximately 0.3% by weight polyacrylate.

11. The composition of claim 2 further comprising a viscosity modifying amount of salt.

12. The composition of claim 11 wherein said salt is selected from the group consisting of univalent and divalent dissociable ionic compounds.

13. The composition of claim 11 wherein said salt is present in a slat-to-polymer ratio of approximately 0.001 to 0.5.

14. The composition of claim 2 further comprising an effective amount of a pharmaceutical medicament or diagnostic compound.

15. The composition of claim 14 wherein said pharmaceutical medicament or diagnostic compound is incorporated in a microparticulate drug delivery system.

16. The composition of claim 14 wherein said pharmaceutical medicament or diagnostic compound is selected from the group consisting of anti-bacterial substances, anti-histamines and decongestants, anti-inflammatories, miotics and anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal compounds, amoebacidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides and lubricating agents.

17. The pharmaceutical composition of claim 2 further comprising a viscosity modifying effective concentration of salt in a salt-to-polymer ratio of 0.045 to 0.075.

18. A drug delivery system comprising the aqueous composition of claim 2 and an effective concentration of an ophthalmic drug.

19. The drug delivery system of claim 18 wherein said ophthalmic drug is incorporated in a microparticulate drug delivery system.

20. The drug delivery system of claim 18 wherein said drug is selected from the group consisting of anti-bacterial substances, anti-histamines and decongestants, anti-inflammatories, miotics and anti-cholinergis, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites anesthetics, anti-fungal compounds, amoebacidal compounds, trichomonacidal agents, analgesics, anti-arthritics, anti-asthmatics, anti-coagulatns, anti-convulsants, anti-depressants, anti-diabetics, anti-neoplastics, anti-psychotics, anti-hypertensive agents, muscle relaxants, proteins, peptides, and lubricating agents.

21. The composition of claim 1 wherein said at least one thermally-sensitive gelling polymer is selected from the group consisting of alkylcellulose, hydroxyalkyl cellulose, block copolymers of polyoxyethylene and polyoxypropylene, and tetrafunctional block polymers of polyoxyethylene and polyoxypropylene and ethylenediamine.

22. The composition of claim 1 wherein said at least one thermally-sensitive gelling polymer is methylcellulose.

23. The composition of claim 1 wherein said at least one pH-sensitive gelling polymer is an acidic polymer.

24. The composition of claim 23 wherein said acidic polymer is a carboxyl containing polymer.

25. The composition of claim 6 wherein said carboxyl containing polymer is polyacrylate.

26. The composition of claim 1 wherein said at least one thermally-sensitive gelling polymer is methylcellulose and said at least one pH-sensitive gelling polymer is polyacrylate.

27. The composition of claim 26 therein said aqueous composition comprises approximately 0.1% to 5% by weight methylcellulose and approximately 0.01% to 10% polyacrylate.

28. The composition of claim 26 wherein said aqueous composition comprises approximately 1% by weight methylcellulose and approximately 0.3% by weight polyacrylate.

29. The composition of claim 1 further comprising a viscosity modifying amount of salt.

30. The composition of claim 29 wherein said salt is selected from the group consisting of univalent and divalent dissociable ionic compounds.

31. The composition of claim 29 wherein said salt is present in a salt-to-polymer ratio of approximately 0.001 to 0.5.

32. The composition of claim 1 further comprising an effective amount of a pharmaceutical medicament or diagnostic compound.

33. The composition of claim 32 wherein said pharmaceutical medicament or diagnostic compound is incorporated in a microparticulate drug delivery system.

34. The composition of claim 32 wherein said pharmaceutical medicament or diagnostic compound is selected from the group consisting of anti-bacterial substances, anti-histamines and decongestants, anti-inflammatorics, miotics and anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal compounds, amoebacidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides and lubricating agents.

35. The pharmaceutical composition of claim 1 further comprising a viscosity modifying effective concentration of salt in a salt-to-polymer ratio of 0.045 to 0.075.

36. A drug delivery system comprising the aqueous composition of claim 1 and an effective concentration of an ophthalmic drug.

37. The drug delivery system of claim 36 wherein said drug is incorporated in a microparticulate drug delivery system.

38. The drug delivery system of claim 36 wherein said ophthalmic drug is selected from the group consisting of anti-bacterial substances, anti-histamines and decongestants, anti-inflammatorics, miotics and anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal compounds, amoebacidal compounds, trichomonacidal agents, analgesics, anti-arthritics, anti-asthmatics, anti-coagulants, anti-convulsants, anti-depressants, anti-diabetics, anti-neoplastics, anti-psychotics, anti-hypertensive agents, muscle relaxants, proteins, peptides, and lubricating agents.

39. An aqueous injectable drug delivery composition for injection into a body to treat a condition requiring pharmacological treatment or diagnosis comprising the composition of claim 1 and an effective concentration of a drug selected from the group consisting of anti-bacterial substances, anti-histamines and decongestants, anti-inflammatorics, miotics and anti-cholinergics, mydriatics, anti-glaucoma compounds, anti-parasitics, anti-viral compounds, carbonic anhydrase inhibitors, diagnostic agents, ophthalmic agents, chelating agents, immunosuppressive agents, anti-metabolites, anesthetics, anti-fungal compounds, amoebacidal compounds, trichomonacidal agents, analgesics, anti-arthritics, anti-asthmatics, anti-coagulatns, anti-convulsants, anti-depressants, anti-diabetics, anti-neoplastics, anti-psychotics, anti-hypertensive agents, muscle relaxants, proteins, peptides and lubricating agents.

* * * * *